United States Patent [19]

Cary, III

[11] Patent Number: 4,785,808
[45] Date of Patent: Nov. 22, 1988

[54] DISPOSABLE ELECTROLYSIS NEEDLE

[76] Inventor: Harry W. Cary, III, 46 Arnold St., Riverside, R.I. 02915

[21] Appl. No.: 118,792

[22] Filed: Nov. 9, 1987

[51] Int. Cl.⁴ ............................................. A61B 17/41
[52] U.S. Cl. ................................................ 128/303.18
[58] Field of Search ...................... 128/303.13, 303.17, 128/303.18, 303.19, 784

[56] References Cited

U.S. PATENT DOCUMENTS

| | | | |
|---|---|---|---|
| 2,100,116 | 11/1937 | Webb | 128/303.18 X |
| 2,110,733 | 3/1938 | Marton | 128/303.18 |
| 2,516,882 | 8/1950 | Kalom | 128/303.18 X |
| 2,700,975 | 2/1955 | Hopfinger et al. | 128/303.18 |
| 3,035,580 | 5/1962 | Guioguiev | 128/303.18 |
| 3,651,812 | 3/1972 | Samuels | 128/303.18 |
| 3,799,168 | 3/1974 | Peters | 128/303.17 X |
| 3,847,153 | 11/1974 | Weissmen | 128/303.14 |

OTHER PUBLICATIONS

Decker et al., "An Electrocautery Instrument . . . ", 10th Ann. Rocky Mt. Bioeng. Symp., May 1973, pp. 5-10.

Primary Examiner—Lee S. Cohen
Attorney, Agent, or Firm—Robert J. Doherty

[57] ABSTRACT

A disposable electrolysis needle assembly including a molded body having a needle outwardly extending from the forward end thereof. The assembly is further provided with structure to both physically and electrically mount and connect the assembly with an electrolysis instrument.

3 Claims, 1 Drawing Sheet

DISPOSABLE ELECTROLYSIS NEEDLE

BACKGROUND AND OBJECTS OF THE INVENTION

The present invention relates to an improvement in the construction of electrolysis needles of the type to remove unwanted hair.

Presently, most electrolysis needles are of the inherently resterilizable type. Such needles include an extremely fine tip or blade (made of surgical steel wire) which is adapted to be inserted into a hair follicle of the patient alongside a hair shaft in the dermis. This fine tip portion is mechanically clenched or otherwise attached to a larger shank portion (stainless steel or plated brass) in turn adapted to be received into an electrical connection socket in the hand held instrument portion of an overall electrolysis device.

Such devices include, as previously mentioned, the removable needle portion, a hand held portion including a cap which is electrically insulated from the needle, and a low voltage electric radiation current source (radio frequency A.C. or galvanic D.C.) extending through the hand held instrument and in turn adapted to supply such energy to the needle when desired by the electrologist for the intended purpose.

A published article discussing such epilation needles was published in the February 1987 edition of "International Hair Route" by the present inventor. A copy of such article is attached and hereby incorporated in the present specification by specific reference.

Although the epilation process through electrolysis as above described does not necessarily mean contact with patient blood, such is possible and, accordingly, with the increase of blood communicable diseases such as Hepatitis Type B, Aids, etc., there is increased concern involving the use of electrolysis needles. In addition, the protective cap can possibly come in contact with patient body fluids. Accordingly, the present inventor believes there will be an increased demand for disposable or throw away needles with intergrated cap and, accordingly, has devised a needle construction which accomplishes the above result and is further conveniently adapted to be attached to an electrolysis instrument in a functional manner without the necessity of contact with the needle or cap portion thereof.

A further desirable attribute of a disposable needle is that it further presents surfaces such that contact between the patient and the instrument itself is reduced or eliminated and thus reducing or eliminating need the attendant need for instrument sterilization.

These and other objects of the present invention are accomplished by a disposable electrolysis needle assembly comprising an electrical insulating body formed of molded plastic (cap) and including a shaped forward end from which an extremely fine metal needle adapted to be inserted into a hair follicle of the skin of a human patient forwardly extends, said body further including a rearwardly extending shank portion of a regular geometric configuration in turn adapted to extend into a receiving socket in the front of the insulated hand grip portion of an electrolysis instrument, said needle further extending through said body and including a portion outwardly projecting from the shank portion thereof to form an electrical connection with said instrument, said needle and said body integrally connected into a single-use, throw away unit.

Other objects, features and advantages of the invention shall become apparent as the description thereof proceeds when considered in connection with the accompanying illustrative drawings.

DESCRIPTION OF THE DRAWING

In the drawings which illustrate the best mode presently contemplated for carrying out the present invention.

DETAILED DESCRIPTION OF THE INVENTION

Figure 1:
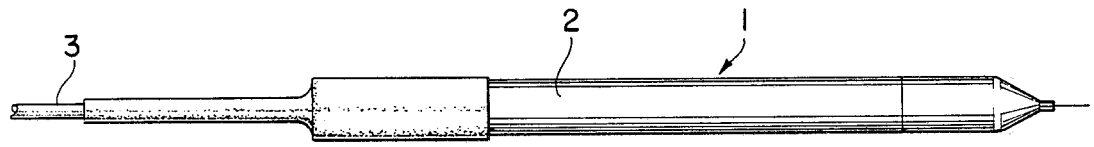
FIG. 1 is an overall elevational view of a standard electrolysis instrument and conventional needle assembly.
Figure 2:
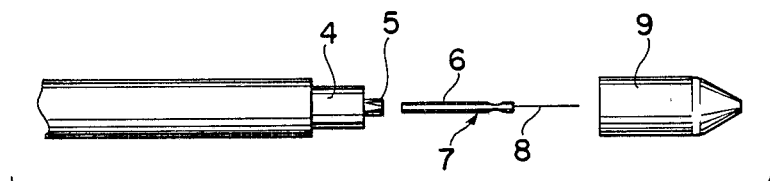
FIG. 2 is an exploded view thereof.

Turning now to the drawings and particularly FIGS. 1 and 2 thereof, a conventional electrolysis instrument is depicted. Such includes an instrument body 2 adapted to be hand held and including a source of power either electrical or electromagnetic through wire 3 attached to the rear thereof. The forward part of the hand held body 2 includes a reduced portion receiving end 4 including a pair of metal clamps 5 into which the enlarged shank portion 6 of a conventional needle assembly 7 having a fine electrolysis needle 8 projecting from the forward end thereof is adapted to be received. In addition, a protective shield or cap 9 is adapted to fit over the forward portion thereof which in turn includes an opening (not shown) through which the needle 8 projects. The cap 9 is adapted to fit on the reduced portion 4 such that the completed assembly 1 is operational.

Turning now to the remaining drawings, the device of the present invention in the form of a composite disposable electrolysis needle assembly 10 is depicted. Such needle assembly 10 includes a needle 12 and a plastic body or cap 14 molded or otherwise assembled as a unit such that they, in effect, form a one-piece construction, that is, they are stored, used, and disposed as a unit. The body 14 preferably has a rounded or dome-shaped configured forward portion 16 from which the forward portion 18 of the needle projects. Such needle portion 18 is the usable portion thereof which enters the patient's hair follicle in the intended manner and may be of the type materials and size as indicated in the aforementioned Cary article.

Figure 4:
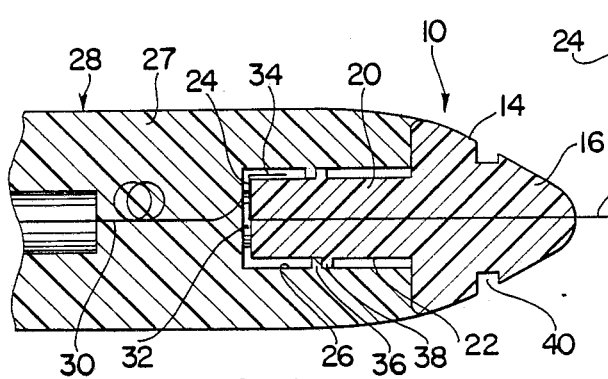
FIG. 4 is a view similar to FIG. 3 but showing the disposable needle assembled in operational contact with an electrolysis instrument.

The rear of the body 14 includes a reduced diameter shank portion 20 having in turn an outer surface 22 and a rear surface 24. Such shank is adapted to be received in an inwardly extending pocket or bore 26 formed in the forward portion of the handle or portion 27 grip of an electrolysis instrument 28. Such instrument 28 includes a source of electrical or electromagnetic power in the form of a conductor wire 30 which extends forwardly through the instrument to a contact plate 32 at the base of the bore 26. The needle 12 in turn is adapted to extend entirely through the body 14 at least to a point where it outwardly projects from the shank 20 in such a manner as to form an appropriate electrical contact with the wire 30 of the instrument 28. As shown in FIG. 4, such electrical contact is by means of the wire 12 extending entirely through the shank 20 to a point where it extends outwardly of the wall 24 at which point a tail portion 34 of the wire 32 extends radially and terminates along a base portion of the outer surface 22.

The assembly 10 may be held into the instrument 28 by any conventional means including frictional fit and including the mating lugs 36, 38 respectively shown on the shank 20 and the bore 26. In that regard, the forward portion 16 of the body may be provided with notches 40 for receipt of a wrench or other instrument by which the assembly 10 can be inserted into the bore 26 in the intended manner. With the lug 36, 38 system, the assembly 10 would be oriented such that the lugs 36 would extend through an opening in the lug or ridge 38 and then be partially rotated to extend therebehind and thus insure an operational fit between the two units. The notches 40 may also contribute to increase the ease by which the assembly 10 may be fitted to the instrument 28 without contacting the forward needle portion 18 by adding a more positive frictional engagement with the electrologist's fingers. So positioned, it is apparent that the instrument 28 may be utilized in the intended manner without necessity of the operator's fingers or hands contacting with the forward portion of the needle 18 and that such portion is shielded from the rest of the instrument 28 by the forward portion 16 of the body 14. Accordingly, any contact with blood or other body fluids of the patient being worked on would only come in contact with the needle 18 of the forward portion 16 of the body. As both these portions are discarded when the needle assembly 10 has been used, the sanitary features of the present invention are accomplished in the intended manner.

Figure 3:
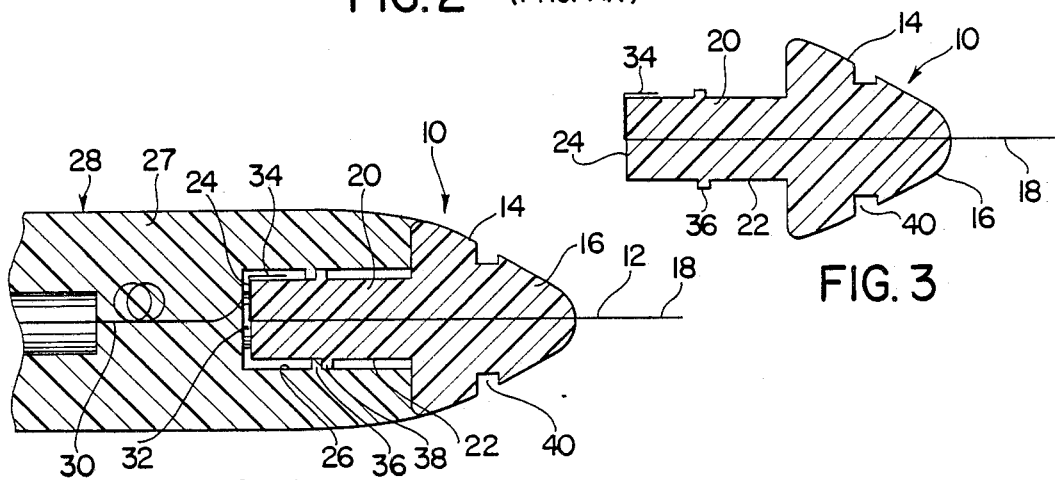
FIG. 3 is an enlarged elevational view of one form of the disposable needle construction of the present invention.
Figure 5:
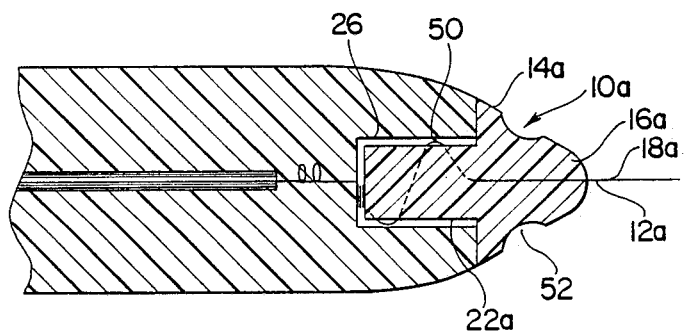
FIG. 5 is a view similar to FIG. 4 but showing a modified form of the invention.

Turning now to FIG. 5 of the drawing, a modified form of the needle assembly 10a is depicted. Such includes the constructions described above in relation to the FIG. 3 and FIG. 4 embodiments, except the rearward extending portions of the needle 12a form a wave-like path such that one or more portions thereof outwardly extend from the outer portion 22a of the shank 20a. Such projections 50 may serve a dual purpose since they may provide the necessary electrical connection with the wall of the bore 26 provided such includes an electrically conductive coating or is otherwise provided with a contact base and provides a slight interference fit with the walls such that the assembly 10a is frictionally held into the instrument pocket 28.

In addition, a circular recess 52 is provided in the forward portion 16a of the body 14a such that finger or tweezer gripping for insertion and removal of the assembly 10a by the electrologist is enhanced.

While there is shown and described herein certain specific structure embodying this invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A disposable electrolysis needle assembly comprising an electrical insulating body formed of molded plastic and including a shaped forward end and an extremely fine uninsulated metal needle adapted to be inserted through the epidermis layer of skin of a human patient outwardly forwardly projecting from said forward end, said body further including a rearwardly extending shank portion of a regular geometric configuration in turn adapted to extend into a receiving socket in the front of the insulated hand grip portion of an electrolysis instrument, said needle further including a wire portion extending through said body and including a portion outwardly projecting from the shank portion thereof so as to form an electrical connection with said instrument, said needle and said body integrally connected into a single-use, throw away unit said shank portion having a base through which said needle wire portion extends to form an electrical contact tail radially extending across at least a portion of said base and wherein said forward end is generally conically-shaped for ease in grasping and said shank portion is in the form of a rearwardly extending generally centrally disposed stem, said stem is of a reduced cross-section with respect to the adjacent generally conically shaped forward end.

2. The needle assembly of claim 1, said needle wire portion including portions outwardly extending from the outer surface of said shank portion.

3. The needle assembly of claim 1, said body forward end including gripping means for increasing the hand manipulativeness of said assembly.

* * * * *